United States Patent [19]
Lucchesi et al.

[11] Patent Number: 6,129,751
[45] Date of Patent: Oct. 10, 2000

[54] CARDIAC LEAD WITH ACTIVE FIXATION AND BIOCOMPATIBLE LUBRICANT

[75] Inventors: Arthur J. Lucchesi, Sugarland; Paul R. Spher; Michael C. Smith, both of Lake Jackson, all of Tex.

[73] Assignee: Intermedics Inc., Angleton, Tex.

[21] Appl. No.: 09/123,659

[22] Filed: Jul. 28, 1998

[51] Int. Cl.$^7$ ........................................ A61N 1/05
[52] U.S. Cl. ..................... 607/127; 607/120; 607/119; 604/175
[58] Field of Search ........................... 607/120, 121, 607/122, 126–130, 119; 600/373–375, 377; 604/174, 175

[56] References Cited

U.S. PATENT DOCUMENTS

| | | |
|---|---|---|
| 4,106,512 | 8/1978 | Bisping . |
| 4,567,901 | 2/1986 | Harris . |
| 5,129,404 | 7/1992 | Spehr et al. . |
| 5,464,404 | 11/1995 | Abela et al. . |
| 5,558,617 | 9/1996 | Heilman et al. . |
| 5,575,787 | 11/1996 | Abela et al. . |
| 5,578,067 | 11/1996 | Eckwall et al. . |
| 5,645,062 | 7/1997 | Anderson et al. . |
| 5,651,785 | 7/1997 | Abela et al. . |
| 5,651,786 | 7/1997 | Abela et al. . |
| 5,782,239 | 7/1998 | Webster, Jr. . |
| 5,782,824 | 7/1998 | Abela et al. . |
| 5,800,334 | 9/1998 | Wilk . |
| 5,919,221 | 7/1999 | Miesel . |
| 5,971,911 | 10/1999 | Wilk . |

OTHER PUBLICATIONS

Intermedics Inc., Temporary Transcutaneous Pacing Wire Extension Lead Model 366–02—Sales Brochure, all pages, Oct. 1982.

*Primary Examiner*—George R. Evanisko
*Attorney, Agent, or Firm*—Schwegman, Lundberg, Woessner & Kluth, P.A.

[57] ABSTRACT

A cardiac stimulator lead is provided that includes a connector for connecting to a cardiac stimulator and an insulating sleeve that has a first end coupled to the connector and a second end. The second end has an opening therein. An electrode is positioned in the insulating sleeve and has a piercing member. The electrode is moveable axially from a retracted position to an extended position wherein the piercing member projects from the opening. A conductor wire is disposed in the sleeve and coupled between the connector and the electrode for transmitting electric signals between the cardiac stimulator and the electrode. A lubricant is provided inside the insulating sleeve for lubricating the movement of the electrode. The lubricant reduces the potential for sticking, particularly for silicone lead sleeves.

22 Claims, 5 Drawing Sheets

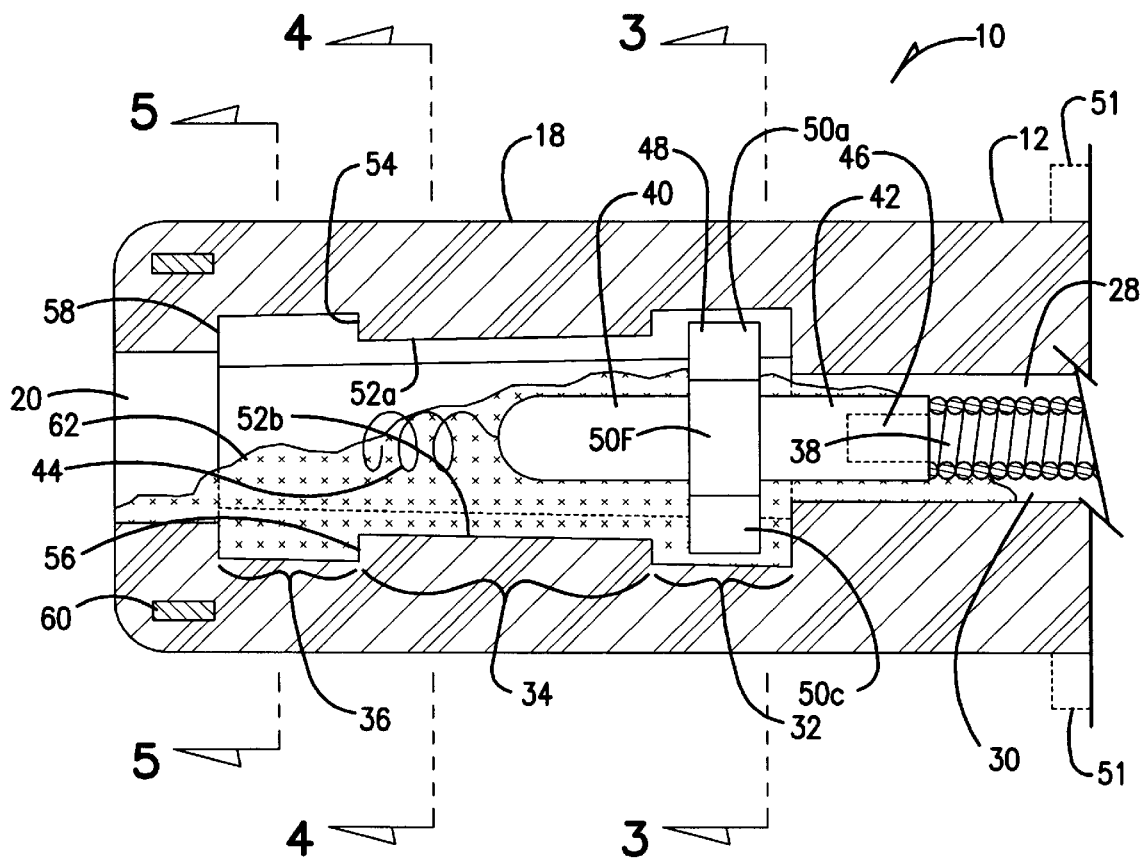
FIG. 2
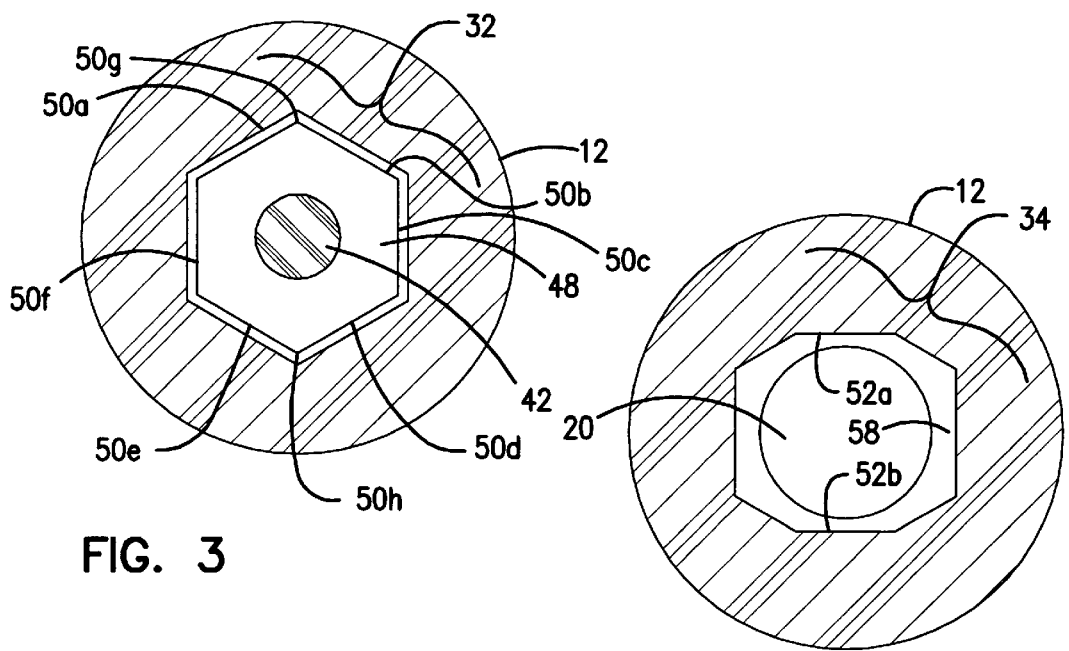
FIG. 3
FIG. 4

CARDIAC LEAD WITH ACTIVE FIXATION AND BIOCOMPATIBLE LUBRICANT

BACKGROUND OF THE INVENTION

1. Field of the Invention

This invention relates generally to cardiac stimulator leads, and more particularly to a cardiac stimulator lead including an extendable and retractable electrode that is lubricated with a biocompatible lubricant.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac stimulator and the incision is closed. The implantation route and site are usually imaged in real time by fluoroscopy to confirm proper manipulation and placement of the lead.

A conventional cardiac stimulator lead normally consists of an elongated flexible tubular, electrically insulating sleeve that is connected proximally to a connector that is adapted to couple to the header of a cardiac stimulator can. The distal end of the insulating sleeve includes some type of tip electrode. To ensure that physical contact with the desired myocardial tissue is maintained after implantation, tip electrodes for most conventional leads are anchored to myocardial tissue by a fixation mechanism of one sort or another. In some leads, a corkscrew-like member is projectable from the sleeve and penetrates the endocardium. In others, the electrode is fitted with one or more radially projecting tines that engage the normally irregular surface of the endocardium. Still others may employ both types of structures.

Some conventional active fixation leads incorporate an axially moveable member that holds or is otherwise coupled to the corkscrew. The moveable member must be moved axially relative to the insulating sleeve to deploy the corkscrew. This is normally accomplished by inserting a stylet into the lead, engaging the moveable member, and applying a thrust to the stylet.

Conventional cardiac lead insulating sleeves are typically composed of biocompatible materials with sufficient flexibility to enable the lead to readily conform to the often irregular transvenous pathway from the cardiac stimulator to the endocardium. Silicone and polyurethane are two commonly used materials. Biocompatibility and superior flexibility over polyurethane has made, and continues to make silicone a frequent choice of lead designers. Silicone presents some mechanical properties that benefit the function of many silicone lead sleeves. A silicone lead sleeve exhibits an inherent tackiness that produces an adhesive-like effect on the surfaces of other structures come into contact with the sleeve. This inherent tackiness is helpful in preventing the sliding movement of the sleeve relative to other structures that are intended to remain in a fixed position relative to the sleeve. Examples of such include the lead connector and a suture sleeve (at least at the incision is closed). However, the inherent tackiness may also impede the function of many types of conventional leads. In many conventional lead designs, it is desirable and necessary to move a member that is in contact with the silicone sleeve. For example, where the lead employs active fixation in the form of a corkscrew coupled to an axially moveable member, the member must be moved relative to the sleeve to deploy the corkscrew. If the member is direct contact with the silicone sleeve, the movement may be significantly impeded by the adhesive-like character of the silicone.

Brute force may be employed in an attempt to dislodge a sticking corkscrew member. For example, the stylet may be repeatedly pushed and pulled and/or the lead tip may be massaged by hand. However, conventional leads are minute devices so these techniques present the risk of damaging the small, delicate structures in the sleeve and corkscrew member. A radiographic marker, if present in the lead, may be damaged as well.

If a sticking corkscrew member is encountered during assembly testing, the entire lead must often be scrapped if the aforementioned manual procedures do not release the corkscrew member. If a sticking problem is encountered at the time of implantation, the implanting physician will, in most cases, discard the lead in favor of devoting time and effort to dislodging the corkscrew member.

The problem of silicone sticking transcends structures positioned inside the lead. For example, suture sleeves sometimes stick to the outer surfaces of lead sleeves and complicate the implantation procedure. The advent of epicardial implantation by trocar introducer in lieu of median sternotomy or thoracotomy also presents the potential for silicone sticking. In this type of implantation procedure the silicone lead sleeve is inserted through a tubular trocar introducer into the chest cavity. The procedure may be impeded if the silicone sleeve sticks to the inner wall of the trocar introducer.

The present invention is directed to overcoming or reducing the effects of one or more of the foregoing disadvantages.

SUMMARY OF THE INVENTION

In accordance with one aspect of the present invention, a cardiac stimulator lead is provided. The cardiac stimulator lead includes a connector for connecting to a cardiac stimulator and an insulating sleeve that has a first end coupled to the connector and a second end. The second end has an opening therein. An electrode is positioned in the insulating sleeve and has a piercing member. The electrode is moveable axially from a retracted position to an extended position wherein the piercing member projects from the opening. A conductor wire is disposed in the sleeve and coupled between the connector and the electrode for transmitting electric signals between the cardiac stimulator and the electrode. A lubricant is provided inside the insulating sleeve for lubricating the movement of the electrode.

In accordance with another aspect of the present invention, a cardiac stimulator lead is provided. The cardiac stimulator lead includes a connector for connecting to a cardiac stimulator and an insulating sleeve that has a first end coupled to the connector and a second end. The second end has an opening therein. A member is positioned in the insulating sleeve and has a piercing member. The member is moveable axially from a retracted position to an extended position wherein the piercing member projects from the opening. An electrode is coupled to the insulating sleeve. A conductor wire is disposed in the sleeve and coupled between the connector and the electrode for transmitting electric signals between the cardiac stimulator and the electrode. A lubricant is provided inside the insulating sleeve for lubricating the movement of the member.

In accordance with another aspect of the present invention, a cardiac lead assembly is provided. The cardiac lead assembly includes a cardiac lead, a tubular introducer for guiding the cardiac lead into a body cavity, and a lubricant to lubricate the sliding movement of the cardiac lead through the tubular introducer.

BRIEF DESCRIPTION OF THE DRAWINGS

The foregoing and other advantages of the invention will become apparent upon reading the following detailed description and upon reference to the drawings in which:

FIG. 2 is a cross-sectional view of FIG. 1 taken at section 2—2 in accordance with the present invention;

FIG. 3 is a cross-sectional view of FIG. 2 taken at section 3—3 in accordance with the present invention;

FIG. 4 is a cross-sectional view of FIG. 2 taken at section 4—4 in accordance with the present invention;

DETAILED DESCRIPTION OF SPECIFIC EMBODIMENTS

Figure 1:
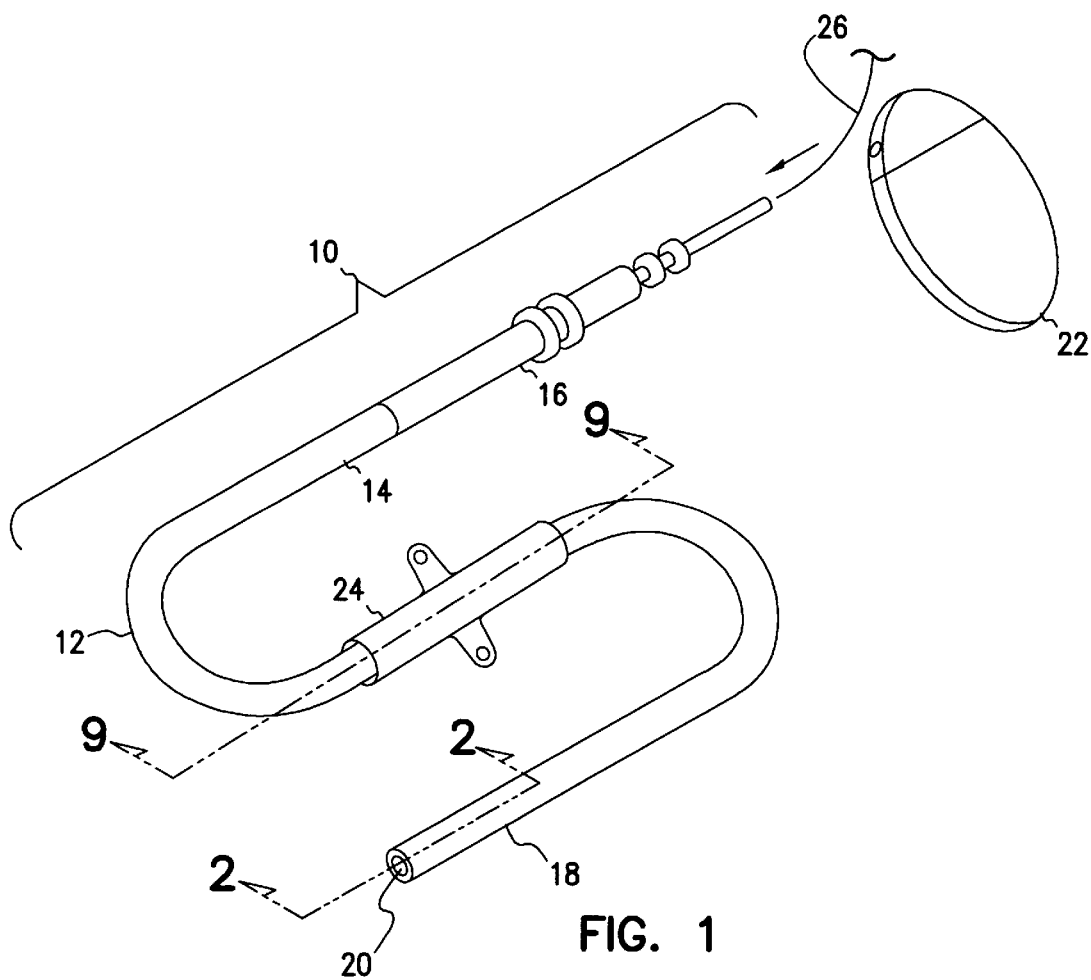
FIG. 1 is a pictorial view of an exemplary embodiment of a cardiac stimulator lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 terminating in a circular opening 20. The connector 16 is designed to be inserted into a cardiac stimulator 22, and is shown highly exaggerated in size relative to the cardiac stimulator 22. The cardiac stimulator 22 may be a pacemaker, a cardioverter/defibrillator, or other type of stimulator or a sensing instrument. A suture sleeve 24 is slipped over the sleeve 12. During implantation, the suture sleeve 24 is sewn to body tissue at the site of transvenous entry. The connector 16 is hollow to enable a flexible stylet 26 to be inserted therein as indicated by the arrow. The stylet 26 is used to spatially manipulate the lead 10 in situ.

The sleeve 12 is a flexible tubular member that provides a robust, electrically insulating coupling between the connector 16 and the electrode 20. The sleeve 12 protects one or more fine gage conductor wires enclosed therein from body fluids and tissues, and is advantageously composed of a biocompatible, electrically insulating material, such as silicone, polyurethane, or like materials.

Figure 5:
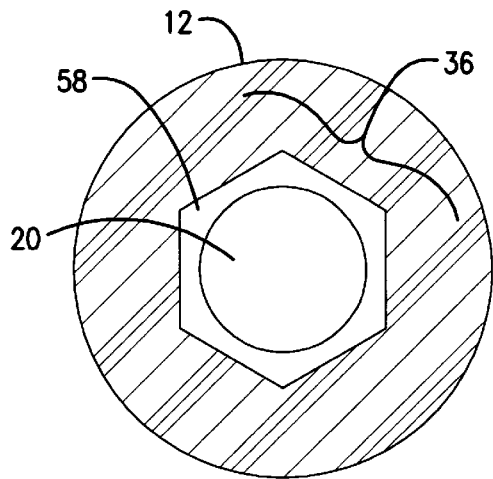
FIG. 5 is a cross-sectional view of FIG. 2 taken at section 5—5 in accordance with the present invention.

The detailed structure of the distal end 18 of the lead 10 may be understood by referring now to FIG. 2, which is a cross-sectional view of FIG. 1 taken at section 2—2, and to FIGS. 3, 4 and 5, which are, respectively, cross-sectional views of FIG. 2 taken at sections 3—3, 4—4 and 5—5. The insulating sleeve 12 is molded with a centrally disposed lumen 28 which is subdivided in the distal end 18 into a proximal section 30, an intermediate section 32, an intermediate section 34, and a distal section 36 that terminates with the opening 20. The proximal section 30 extends from the connector 16 to the intermediate section 32 and has a generally circular cross-section that is dimensioned to accommodate a coiled conductor wire 38 that is attached proximally to the connector 16 by welding, crimping or like methods. As best seen in FIG. 3, the intermediate section 32 is molded with a generally hexagonal cross-section.

Figure 6:
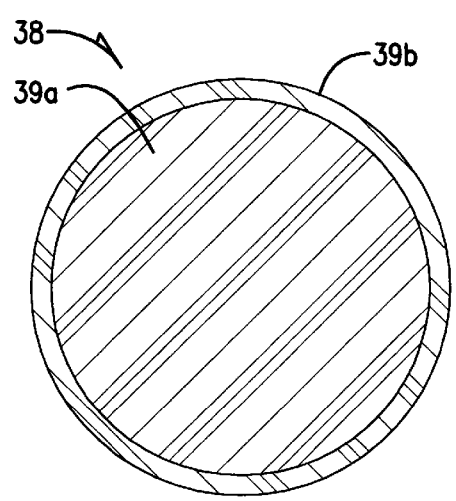
FIG. 6 is a magnified cross-sectional view of a conductor wire of the lead shown in FIGS. 1 and 2 in accordance with the present invention.

The detailed structure of the conductor wire 38 may be understood by referring now to FIG. 6, which is a magnified cross-sectional view. The wire 38 includes a conductor 39a individually coated with an insulating jacket 39b. The conductor 39a may be composed of a variety of biocompatible conducting materials, such as MP35N, stainless steel, or like materials. The insulating jacket 39b may be composed of a variety of biocompatible insulating materials, such as ETFE (fluoropolymer resin) or like materials. The skilled artisan will appreciate that another form of conductor wire may be used, such as an uninsulated wire.

Referring again to FIGS. 2, 3, 4 and 5, the intermediate section 32 is molded with a generally hexagonal cross-section and is inwardly tapered, that is, decreases from a maximum diameter at the transition from the proximal section 30 to a smaller diameter nearer the intermediate section 34. An extendable/retractable member or tip electrode 40 (hereinafter "electrode 40") is positioned inside the insulating sleeve 12 and is moveable from a retracted position in the intermediate section 32 shown in FIG. 2 to an extended position depicted in a later figure, and vice versa. The electrode 40 includes a tubular shank 42 that is connected proximally to the conductor wire 38 by welding, crimping or like techniques, and terminates distally in an active fixation piercing member or corkscrew 44. The proximal end of the shank 42 includes a tubular bore 46 shown in phantom to receive the distal end of the stylet 26 for extension and retraction purposes to be described below. A flange 48 is coupled to or integrally formed with the shank 42. The flange 48 has a generally hexagonal cross-section that defines six peripherally spaced, flat outer surfaces 50a, 50b, 50c, 50d, 50e, and 50f, six axially extending edges, two of which are designated 50g and 50h. The flange 48 is fabricated with a maximum outer diameter, that is, the maximum distance from opposing surfaces, such as the surfaces 50a and 50d, that is smaller than the minimum inner dimension of the intermediate section 32 so that the electrode 40 may be readily moved axially therethrough.

The electrode 40 is designed to function both as a carrier for the corkscrew 44 and as a conductor to convey electrical signals between myocardial tissue and the conductor wire 38. Accordingly, the electrode 40 may composed of a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material. The skilled artisan will appreciate that the two functions could be performed by separate structures, that is, the electrical conducting function could be performed by a fixed electrode coupled to the distal end 18 and tied to the conductor wire 38, such as the annular electrode 51 shown in phantom in FIG. 2, and the member presently identified as the electrode 40 could be used only as a carrier for the corkscrew 44. In this alternative, the electrode 51 may be composed of any of the aforementioned conducting or semiconductor materials, and the member presently identified as the electrode 40 may be fabricated from the same materials, or from non-conducting biocompatible materials, such as polyimide, polyurethane or like materials.

The corkscrew 44 is advantageously composed of the same types of materials used to fabricate the electrode 40, and is coated with a biocompatible coating, such as parylene C or like materials. Alternatively, the corkscrew 44 may be uncoated and form part of the electrical stimulation/sensing pathway.

The intermediate section 34 is molded with a generally octagonal cross-section that defines eight flat, peripherally spaced surfaces, two of which are designated 52a and 52b. Like the intermediate section 32, the intermediate section 34 is inwardly tapered. The inwardly tapered profile and the octagonal cross-section of the intermediate section 34 provide a mechanical barrier against the unintentional axial movement of the electrode 40 into the distal section 36. The surfaces 52a and 52b, in particular, are designed to provide a compliant barrier against the passage of the edges 50g and 50h of the flange 48. The combined barriers to sliding movement ensure that the electrode 40 will only project from the sleeve 12 when intentionally thrust distally by the implanting physician as described below. The distal ends of the surfaces 52a and 52b include distally facing shoulders 54 and 56.

The distal section 36 is a mirror image of the intermediate section 32 with the same general inwardly tapering hexagonal cross-section. Like the intermediate sections 32 and 34, the distal section 36 tapers down to a smaller diameter nearer the opening 20 to aid in retaining the electrode 40 in the sleeve 12 and to establish a friction fit between the electrode 40 and the section 36 sot that the electrode 40 will rotate with the lead 10. The distal section 36 terminates with the circular opening 20. The circular opening 20 is provided with a smaller diameter than the inner diameter of the intermediate section 36 to define a proximally facing shoulder 58 against which the flange 48 may abut when the electrode 40 is moved to the extended position as described below. To facilitate imaging, an annular radiographic marker 60 may be molded into the distal end 18 of the insulating sleeve 12.

The skilled artisan will appreciate the various cooperating members, such as the flange 48 and the sections 32, 34 and 36 may be fabricated with other than hexagonal and octagonal cross-sections. A myriad of shapes may be used so long as there is some restriction to the inadvertent axial movement of the electrode 40 to the extended position.

Figure 7:
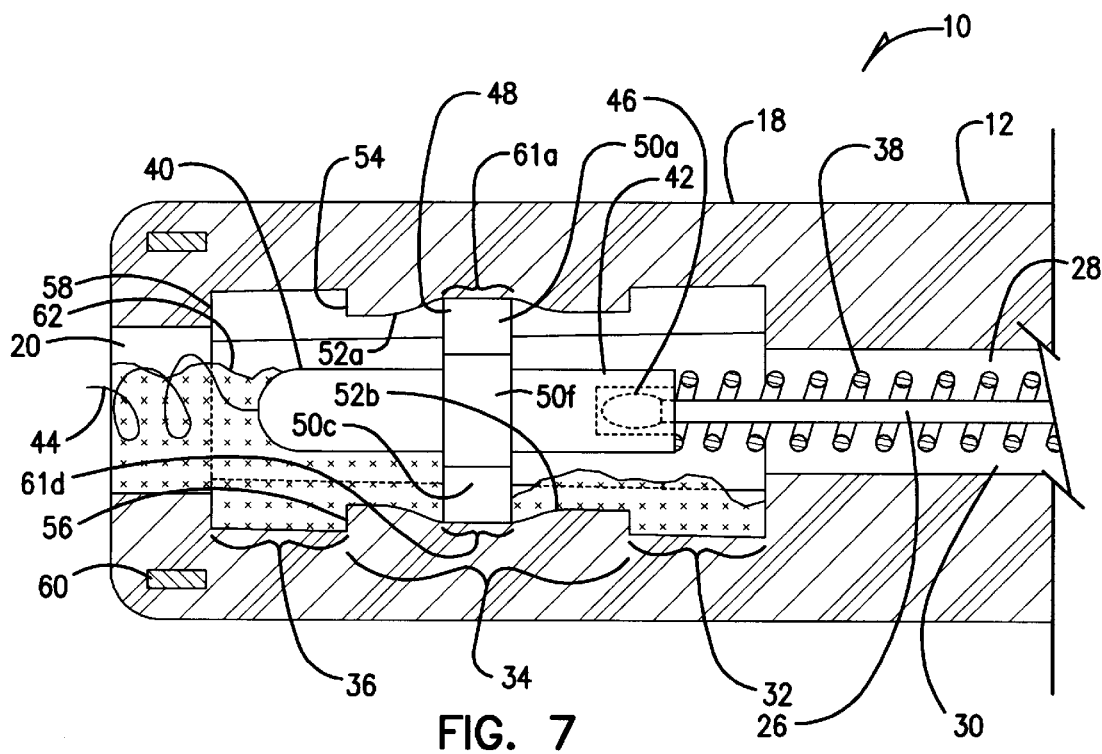
FIG. 7 is a cross-sectional view like FIG. 2 depicting partial extension of an extendable/retractable electrode in accordance with the present invention.
Figure 8:
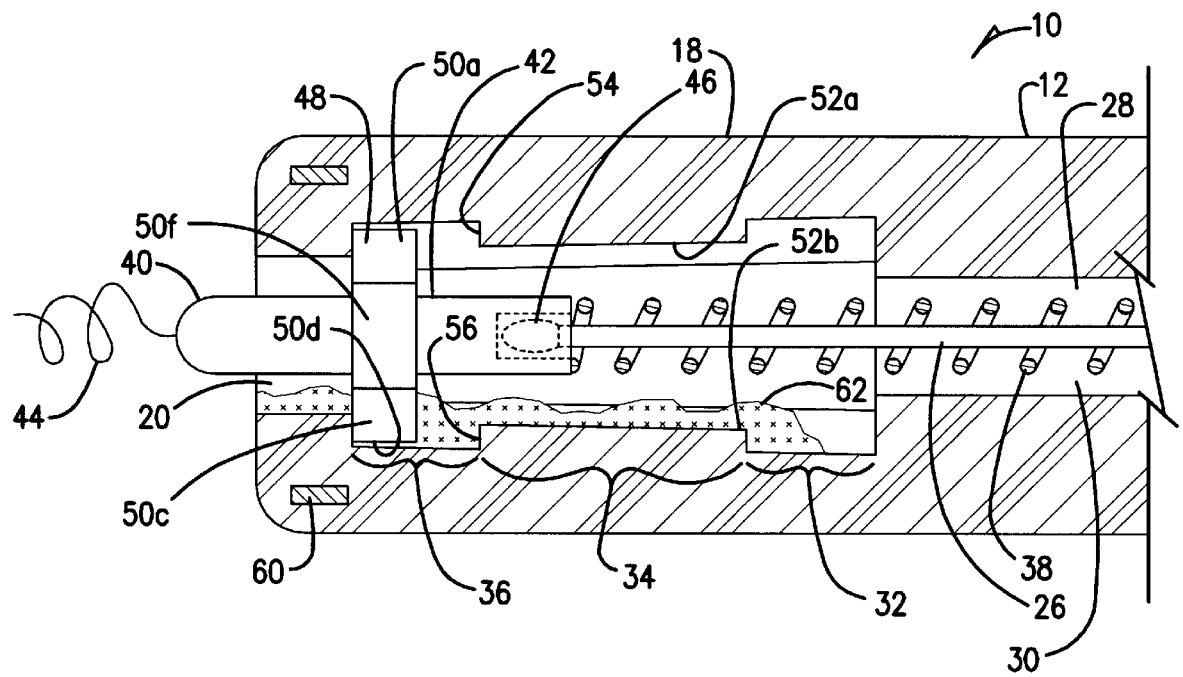
FIG. 8 is a cross-sectional view like FIG. 2 depicting full extension of the extendable/retractable electrode in accordance with the present invention.

The extension and retraction of the electrode 40 may be understood by referring now to FIGS. 2, 7 and 8. FIGS. 7 and 8 are cross-sectional views like FIG. 2 depicting movement of the electrode 40 from the retracted position to an extended position. The stylet 26 is introduced into the lumen 18 and inserted into the bore 46 of the shank 42. The stylet 26 is provided with structure to engage the bore 46. The structure may be a bulbous tip as shown, that provides an interference fit with the bore 46, or a set of threads (not shown) to engage a corresponding set of threads formed in the bore (not shown), or other suitable fastening structure. A thrust is imparted on the stylet 26 to move the electrode 40 axially into the intermediate section 34. As the flange 48 enters the intermediate section 34, the surfaces 50a, 50b, 50c, 50d, 50e, and 50f respectively engage the flat surfaces of the intermediate section 34, particularly the surfaces 52a and 52b. As a result of the compliant character of the insulating sleeve 12, the axial movement of the flange 48 through the intermediate section 34 deforms the flat surfaces of the section 34 radially outwardly. The outward deformations of two of the surfaces, namely 52a and 52b, are indicated generally at 61a and 61d in FIG. 7.

The axial movement of the flange 48 through the intermediate section 34 is resisted both by the mechanical friction associated with the deformation of the flat surfaces, particularly 52a and 52b and, as noted above, the inherent tackiness of silicone. The magnitude of the resistance is a function of a variety factors, such as the condition of the silicone and the tolerances of the sliding parts, among others. The resistance due to silicone adhesion may be significant, particularly where the lead 10 has been packaged for a number of years prior to implantation. This stems from the fact that silicone may harden and actually form an adhesive-like bond with the exterior surface of the electrode 40 after lengthy periods of time in storage.

Regardless of the particular origin, the mechanical resistance must be overcome on at least two occasions in order for the lead 10 to be successfully implanted. During post-assembly testing the stylet 26 is inserted to test the movement of the electrode 40. If the electrode 40 resists movement at this stage, the stylet 26 may be pushed and pulled a few times in an attempt to dislodge the electrode 40. However, it is desirable to avoid applying excessive thrust on the stylet 26 to avoid damaging the sleeve 12, the radiographic marker 60 and/or the electrode 40. If that method fails, the distal end 18 may be massaged, albeit at the risk of damaging the lead 10. If massaging fails, the lead 10 is usually discarded. If the electrode 40 cannot be readily moved at the time of implantation, the implanting physician usually discards the lead 10 in favor of attempting to pry the electrode 40 loose by massaging the distal end 18 or by forceful movements of the stylet 26.

Conventional cardiac leads do not incorporate a lubricant to facilitate the sliding movement of one tubular structure, such as the flange 48, through another, such as the section 34. In these conventional leads, reliance is placed on the aforementioned brute force methods to dislodge a sticking electrode.

In contrast to conventional lead designs, the lead 10 is provided with lubricant to facilitate the passage of the electrode 40 through the intermediate section 34. The lubricant is designated by the number 62 and the multiplicity of small "x's" in FIGS. 2, 7 and 8. The lubricant advantageously exhibits a low viscosity at temperatures ranging at least from room temperature to body temperature (about 20 to 37° C.), long shelf-life, and biocompatibility. In an exemplary embodiment, the lubricant 62 is polyethylene glycol ("PEG") 400, where the number "400" indicates the approximate average molecular weight in grams/mole (g/mole). A range of average molecular weights may be used, such as about 200 to about 600 g/mole.

The lubricant 62 may be injected into the lumen 28 via the opening at the time of assembly. As a result of the relatively low viscosity of the lubricant 62 and the capillary action of the lumen 28, the lubricant 62 will tend to migrate from the opening 20 to some distance into or past the proximal section 30, and pool in the points of lowest elevation in the lumen 28 as shown in FIG. 2. Accordingly, the stylet 26 should be rotated prior to moving the electrode 40 axially so that the entire exterior surface of the flange 48 may be bathed in the lubricant 62.

As the electrode 40 is moved through the intermediate section 34, a volume of the lubricant 62 may be captured and discharged out of the opening 20 as shown in FIG. 7. Referring now to FIG. 8, the stylet 26 is advanced farther into the insulting sleeve 12 until the flange 48 clears the intermediate section 34 and the distal portion of the shank 42 projects through the opening 20. At this point, the entire lead 10 may be twisted to screw the corkscrew 44 into myocardial tissue. The friction fit of the flange 48 in the distal section 36 ensures that the electrode 40 and corkscrew 44 rotate with the lead 10. The distally facing shoulders 54 and 56 ensure that the electrode will not inadvertently move axially back into the intermediate section 34.

If it is desired to withdraw the lead 10, the lead 10 may be twisted to disengage the corkscrew 44 from myocardial tissue and pulled out of the body. If desired, the electrode 40 may be returned to the retracted position shown in FIG. 2 prior to extraction of the lead 10 from the body by engaging and pulling the electrode 40 with the stylet 26.

The presence of the lubricant 62 not only serves to lubricate the movement of the electrode 40, but also two other important functions. First, the volume of the lubricant 62 in the distal section 36, and the intermediate sections 34 and 32 serves as a temporary barrier against the intrusion of body fluids into the lumen 18, which might otherwise migrate through the lead sleeve 12 and flow out of the connector 16. It is desirable to prevent the flow of body fluids out of the connector 16 so that connector 16 will not require cleaning prior to connection with the cardiac stimulator 22 (See FIG. 1), and so that a poor electrical connection due to contamination is avoided. Second, a temporary blockage of the lumen 28 serves to prevent the influx of air into the lumen 28 from the connector 16 which might otherwise discharge into the heart. The blockage will be temporary where PEG is used as the lubricant 62, as PEG is both water and blood soluble.

It is anticipated that the body dissolvable character of PEG may also aid in reducing the thresholds of the electrode 40 by eliminating contaminants from the surface thereof. During fabrication of the lead 10, various contaminants may adhere to the exterior of the electrode 40 and remain even after sterilization of the lead 10 by exposure to ethylene oxide or other commonly used sterilants. It is anticipated that the dissolution of the PEG may aid in liberating such materials that remain on the electrode 40 following sterilization. This enhanced cleanliness may reduce the threshold voltages required at the time of implant.

The solubility of the PEG lubricant may also be used as a drug eluding matrix to provide in situ therapy of myocardial tissue immediately surrounding the tip electrode 40. For example, an anti-inflammatory agent, such as a steroid, may be mixed with the lubricant 62 and be absorbed into myocardial tissue as the lubricant 62 is dissolved by body fluids.

Figure 9:
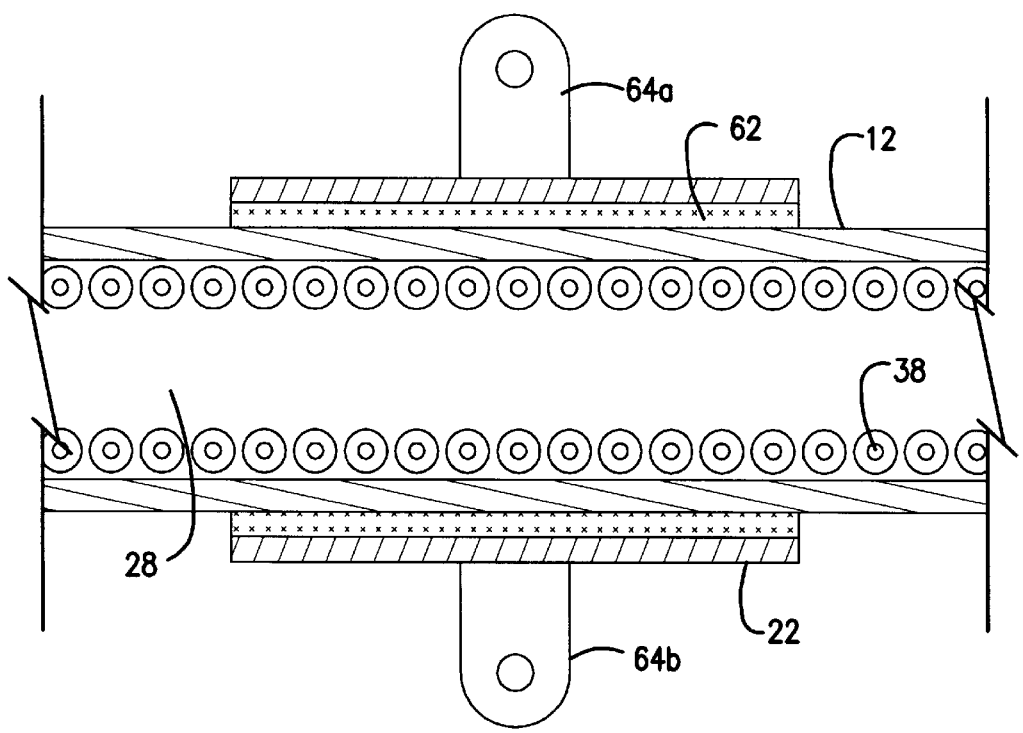
FIG. 9 is a cross-sectional view of FIG. 1 taken at section 9—9 in accordance with the present invention.

The concept of providing PEG as a lubricant between the sliding surfaces of two members of an implantable cardiac lead may be applied to a variety of different sliding structures. One exemplary embodiment is illustrated in FIG. 9, which is a cross-sectional view of FIG. 1 taken at section 9—9. FIG. 9 depicts a close-up cross-sectional view of the insulating sleeve 12 as well as the suture sleeve 22. The suture sleeve 22 includes first and second suture wings 64a and 64b, which are not shown in section. As noted above, in conventional cardiac lead designs, there may be occasional sticking between the interior surface of the suture sleeve 22 and the exterior surface of the insulating sleeve 12. This is commonly due to the inherent tackiness of silicone and is exacerbated when both the insulating sleeve 12 and the suture sleeve 22 are composed of silicone. In contrast to conventional designs, the illustrated embodiment in FIG. 9 is provided with a volume 62 of PEG, such as PEG 400, between the interior surface of the suture sleeve 22 and the exterior of the insulating sleeve 12. The lubricant 62 may be applied to the exterior of the sleeve 12 or the interior surface of the suture sleeve 22 or both as desired.

Figure 10:
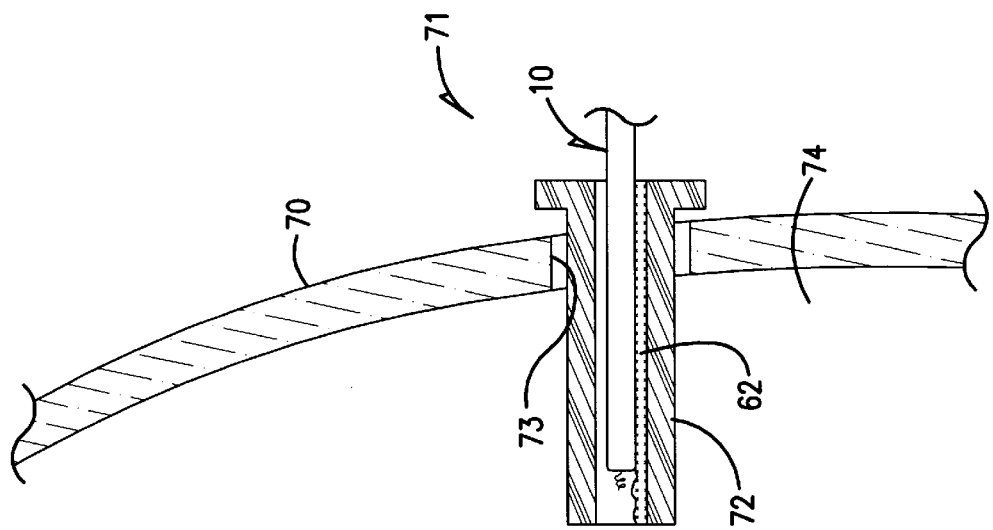
FIG. 10 is a cross-sectional view of an exemplary cardiac lead assembly including a lubricated tubular introducer in accordance with the present invention.
Figure 10:
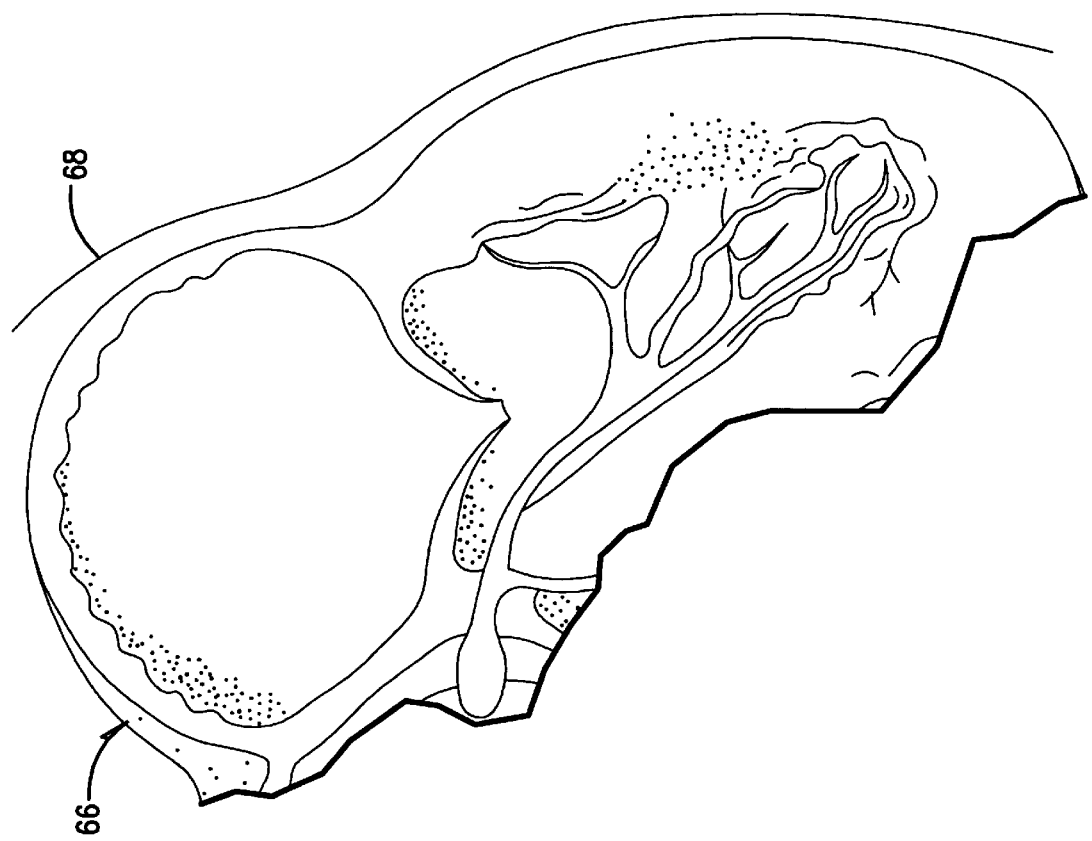

The use of a lubricant, such as PEG 400, may be incorporated into other situations involving the relative sliding movement of tubular structures in cardiac lead systems. FIG. 10 depicts a cross-sectional view of another exemplary embodiment in accordance with the present invention incorporating the use of a PEG lubricant, such as PEG 400, to facilitate the relative sliding movement of two such tubular structures. FIG. 10 depicts a cross-sectional view of the left side of a heart 66 protected by a portion of the pericardial sack 68. A portion of the chest wall 70 is shown in section without separate delineation of any ribs. A cardiac lead assembly 71 is provided that includes the cardiac lead 10, a tubular introducer or trocar 72 and the lubricant 62. An incision 73 is made through the chest wall 70 to allow the insertion of the introducer 72 through the chest wall 70 and into the chest cavity 74. The introducer 72 is used to facilitate epicardial fixation of the cardiac lead 10. In such circumstances, it is desirable for the implanting physician to be able to readily slide the lead 10 through the introducer 72. Easy sliding movement enhances the tactile response of the lead 10 and enables the implanting physician to make delicate and precise movements of the lead 10 when necessary to precisely place the lead 10 near a particular portion of the heart. In this regard, the lubricant, again indicated generally at 62 and shown by the multiplicity of small "x's", is dispersed either on the exterior of the lead 10 or the interior of the introducer 72 or both. Where it is anticipated that the lubricant 62 will not fill the entire volume of the introducer 72, the lead 10 may be twisted by the physician to insure a uniform coating of the lead 10.

The illustrated insertion path for the cardiac lead assembly 71 is through the chest wall 70 and into the chest cavity 74 proximate the heart 66. However, the skilled artisan will appreciate that the insertion point may be into another body cavity as desired.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac stimulator lead, comprising:
   a connector for connecting to a cardiac stimulator;
   an insulating sleeve having a first end coupled to the connector and a second end, the second end having an opening therein;

an electrode positioned in the insulating sleeve and having a piercing member, the electrode being moveable axially from a retracted position to an extended position wherein the piercing member projects from the opening;

a conductor wire disposed in the sleeve and coupled between the connector and the electrode for transmitting electric signals to the electrode;

a lubricant inside the insulating sleeve for lubricating the movement of the electrode; and a drug mixed with the lubricant.

2. The cardiac stimulator lead of claim 1, wherein the insulating sleeve is composed of silicone.

3. The cardiac stimulator lead of claim 1, wherein the lubricant comprises polyethylene glycol.

4. The cardiac stimulator lead of claim 3, wherein the polyethylene glycol has an average molecular weight of about 200 to about 600 g/mole.

5. The cardiac stimulator lead of claim 1, wherein the conductor wire comprises a conductor coated with an insulating jacket.

6. The cardiac stimulator lead of claim 1 wherein the drug comprises an anti-inflammatory agent.

7. The cardiac stimulator lead of claim 1, comprising a suture sleeve positioned around the insulating sleeve with the lubricant being dispersed between the exterior of the insulating sleeve and the interior of the sleeve.

8. A cardiac stimulator system comprising the cardiac stimulator lead of claim 1, and a cardiac stimulator coupled to the connector.

9. A cardiac stimulator lead, comprising:

a connector for connecting to a cardiac stimulator;

an insulating sleeve having a first end coupled to the connector and a second end, the second end having an opening therein;

a member positioned in the insulating sleeve and having a piercing member, the member being moveable axially from a retracted position to an extended position wherein the piercing member projects from the opening;

an electrode coupled to the insulating sleeve;

a conductor wire disposed in the sleeve and coupled between the connector and the electrode for transmitting electric signals to the electrode;

a lubricant inside the insulating sleeve for lubricating the movement of the member; and a drug mixed with the lubricant.

10. The cardiac stimulator lead of claim 9, wherein the insulating sleeve is composed of silicone.

11. The cardiac stimulator lead of claim 9, wherein the lubricant comprises polyethylene glycol.

12. The cardiac stimulator lead of claim 11, wherein the polyethylene glycol has an average molecular weight of about 200 to about 600 g/mole.

13. The cardiac stimulator lead of claim 9, wherein the conductor wire comprises a conductor coated with an insulating jacket.

14. The cardiac stimulator lead of claim 9 wherein the drug comprises an anti-inflammatory agent.

15. The cardiac stimulator lead of claim 9, comprising a suture sleeve positioned around the insulating sleeve with the lubricant being dispersed between the exterior of the insulating sleeve and the interior of the suture sleeve.

16. A cardiac stimulator system comprising the cardiac stimulator lead of claim 9, and a cardiac stimulator coupled to the connector.

17. A cardiac lead comprising:

a connector for connecting to a cardiac stimulator;

an insulating sleeve having a first end coupled to the connector and a second end, the second end having an opening therein;

an electrode positioned in the insulating sleeve and having a piercing member, the electrode being moveable axially from a retracted position to an extended position wherein the piercing member projects from the opening;

a conductor wire disposed in the sleeve and coupled between the connector and the electrode for transmitting electric signals to the electrode; and a lubricant inside the insulating sleeve for lubricating the movement of the electrode, wherein the lubricant comprises polyethylene glycol.

18. The cardiac lead of claim 17, wherein the polyethylene glycol has an average molecular weight of about 200 to about 600 g/mole.

19. A cardiac lead comprising:

a connector for connecting to a cardiac stimulator;

an insulating sleeve having a first end coupled to the connector and a second end, the second end having an opening therein;

an electrode positioned in the insulating sleeve and having a piercing member, the electrode being moveable axially from a retracted position to an extended position wherein the piercing member projects from the opening;

a conductor wire disposed in the sleeve and coupled between the connector and the electrode for transmitting electric signals to the electrode;

a lubricant inside the insulating sleeve for lubricating the movement of the electrode; and a suture sleeve positioned around the insulating sleeve with the lubricant being dispersed between the exterior of the insulating sleeve and the interior of the suture sleeve.

20. A cardiac lead comprising:

a connector for connecting to a cardiac stimulator;

an insulating sleeve having a first end coupled to the connector and a second end, the second end having an opening therein;

a member positioned in the insulating sleeve and having a piercing member, the member being moveable axially from a retracted position to an extended position wherein the piercing member projects from the opening;

an electrode coupled to the insulating sleeve;

a conductor wire disposed in the sleeve and coupled between the connector and the electrode for transmitting electric signals to the electrode;

a lubricant inside the insulating sleeve for lubricating the movement of the electrode; wherein the lubricant comprises polyethylene glycol.

21. The cardiac lead of claim 20, wherein the polyethylene glycol has an average molecular weight of about 200 to about 600 g/mole.

22. A cardiac lead comprising:

a connector for connecting to a cardiac stimulator;

an insulating sleeve having a first end coupled to the connector and a second end, the second end having an opening therein;

a member positioned in the insulating sleeve and having a piercing member, the member being moveable axially from a retracted position to an extended position wherein the piercing member projects from the opening;

an electrode coupled to the insulating sleeve;

a conductor wire disposed in the sleeve and coupled between the connector and the electrode for transmitting electric signals to the electrode;

a lubricant inside the insulating sleeve for lubricating the movement of the electrode; and a suture sleeve positioned around the insulating sleeve with the lubricant being dispersed between the exterior of the insulating sleeve and the interior of the suture sleeve.

* * * * *